US008895743B2

(12) United States Patent
Wu et al.

(10) Patent No.: US 8,895,743 B2
(45) Date of Patent: Nov. 25, 2014

(54) METHYSERGIDE DERIVATIVES

(71) Applicant: Map Pharmaceuticals, Inc., Mountain View, CA (US)

(72) Inventors: Libo Wu, Mountain View, CA (US); Jian Zhang, Mountain View, CA (US)

(73) Assignee: Map Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 14/134,114

(22) Filed: Dec. 19, 2013

(65) Prior Publication Data

US 2014/0179730 A1 Jun. 26, 2014

Related U.S. Application Data

(60) Provisional application No. 61/745,131, filed on Dec. 21, 2012, provisional application No. 61/753,328, filed on Jan. 16, 2013.

(51) Int. Cl.
  *C07D 457/06* (2006.01)
  *C07D 457/04* (2006.01)
  *C07D 471/06* (2006.01)

(52) U.S. Cl.
  CPC .................................. *C07D 471/06* (2013.01)
  USPC ............................................. 546/69; 546/67

(58) Field of Classification Search
  USPC ....................................... 514/288; 546/69, 67
  See application file for complete search history.

(56) References Cited

U.S. PATENT DOCUMENTS

| | | | |
|---|---|---|---|
| 3,048,591 A * | 8/1962 | Lucas ............................. | 546/54 |
| 3,536,809 A | 10/1970 | Applezweig | |
| 3,598,123 A | 8/1971 | Zaffaroni | |
| 3,710,795 A | 1/1973 | Higuchi et al. | |
| 3,833,725 A | 9/1974 | Thompson | |
| 3,845,770 A | 11/1974 | Theeuwes et al. | |
| 3,916,899 A | 11/1975 | Theeuwes et al. | |
| RE28,819 E | 5/1976 | Thompson | |
| 4,008,719 A | 2/1977 | Theeuwes et al. | |
| 4,044,126 A | 8/1977 | Cook et al. | |
| 4,165,376 A * | 8/1979 | Rosenberg ................... | 514/325 |
| 4,328,245 A | 5/1982 | Yu et al. | |
| 4,358,603 A | 11/1982 | Yu | |
| 4,364,923 A | 12/1982 | Cook et al. | |
| 4,409,239 A | 10/1983 | Yu | |
| 4,410,545 A | 10/1983 | Yu et al. | |
| 4,414,209 A | 11/1983 | Cook et al. | |
| 4,522,811 A | 6/1985 | Eppstein et al. | |
| 4,970,314 A * | 11/1990 | Borner et al. .................. | 544/346 |
| 5,033,252 A | 7/1991 | Carter | |
| 5,052,558 A | 10/1991 | Carter | |
| 5,059,595 A | 10/1991 | Le Grazie | |
| 5,073,543 A | 12/1991 | Marshall et al. | |
| 5,120,548 A | 6/1992 | McClelland et al. | |
| 5,323,907 A | 6/1994 | Kalvelage | |
| 5,354,556 A | 10/1994 | Sparks et al. | |
| 5,591,767 A | 1/1997 | Mohr et al. | |
| 5,639,476 A | 6/1997 | Oshlack et al. | |
| 5,639,480 A | 6/1997 | Bodmer et al. | |
| 5,674,533 A | 10/1997 | Santus et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gurewich | |
| 5,840,674 A | 11/1998 | Yatvin et al. | |
| 5,860,957 A | 1/1999 | Jacobsen et al. | |
| 5,891,474 A | 4/1999 | Busetti et al. | |
| 5,900,252 A | 5/1999 | Calanchi et al. | |
| 5,922,356 A | 7/1999 | Koseki et al. | |
| 5,948,433 A | 9/1999 | Burton et al. | |
| 5,972,366 A | 10/1999 | Haynes et al. | |
| 5,972,891 A | 10/1999 | Kamei et al. | |
| 5,980,945 A | 11/1999 | Ruiz | |
| 5,983,134 A | 11/1999 | Ostrow | |
| 5,985,307 A | 11/1999 | Hanson et al. | |
| 5,985,317 A | 11/1999 | Venkateshwaran et al. | |
| 5,993,855 A | 11/1999 | Yoshimoto et al. | |
| 6,004,534 A | 12/1999 | Langer et al. | |
| 6,010,715 A | 1/2000 | Wick et al. | |
| 6,024,975 A | 2/2000 | D'Angelo et al. | |
| 6,039,975 A | 3/2000 | Shah et al. | |

(Continued)

FOREIGN PATENT DOCUMENTS

| | | | |
|---|---|---|---|
| GB | 996062 | * | 6/1965 |
| GB | 996062 A | | 6/1965 |
| WO | WO2005025506 A2 | | 3/2005 |

OTHER PUBLICATIONS

Troxler, F. et al.: Substitution in the ring system of lysergic acid. Substitution on the indole N atom. Helvetica Chimica Acta, vol. 40, pp. 1706-1720, 1957.*
Guillory, Polymorphism in Pharmaceutical Solids, Generation of Polymorphs, Hydrates, Solvates, and Amorphous Solids, 1999, pp. 202-205, Chapter 5, Marcel Dekker, Inc., New York, US.
Howard C. Ansel, Ansel Introduction to Pharmaceutical Dosage Forms, Ansel Introduction to Pharmaceutical Dosage Forms, 2005, 738 pages, Ninth Edition, Wolters Kluwer.
Rockville, MD., The United States Pharmacopeia (USP), USP 25-NF 20, Jan. 2, 2002.

(Continued)

*Primary Examiner* — Charanjit Aulakh
(74) *Attorney, Agent, or Firm* — Jennifer C. Cheng

(57) ABSTRACT

Provided herein are novel methysergide derivatives and compositions thereof. In other embodiments, provided herein are methods of treatment, prevention, or amelioration of a variety of medical disorders or symptoms thereof, such as, migraine and Parkinson's disease using the compounds and compositions disclosed herein. In still other embodiments, provided herein, such as, for example, are methods for antagonizing the $5\text{-HT}_{2B}$ receptor without agonizing the $5\text{-HT}_{2B}$ receptor using the compounds and compositions disclosed herein. In still other embodiments, provided herein such as, for example, are methods of agonizing the $5\text{-HT}_{1A}$ receptor using the compounds and compositions disclosed herein.

3 Claims, No Drawings

(56) References Cited

U.S. PATENT DOCUMENTS

| | | |
|---|---|---|
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,256,533 B1 | 7/2001 | Yuzhakov et al. |
| 6,261,595 B1 | 7/2001 | Stanley et al. |
| 6,264,970 B1 | 7/2001 | Hata et al. |
| 6,267,981 B1 | 7/2001 | Okamoto et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |

OTHER PUBLICATIONS

Troxler, F. et al., Subsitution in the ring system oflysergiv acid. Substitution on the indole N atom, Helvetica Chimica Acta., 1957, pp. 1706-1720, vol. 40.

International Search Report, PCT/US2013/076424, Mar. 28, 2014.

Christopher D. Saudek, et al., A Preliminary Trial of the Programmable Implantable Medication System for Insulin Delivery, The New England Journal of Medicine, Aug. 31, 1989, 574-579, vol. 321 No. 9.

J. Max Goodson, Dental Applications, Medical Applications of Controlled Release, 1984, Chapter 6, p. 115-138, vol. II Applications and Evaluation.

Michael V. Sefton et al., Implant Able Pumps, CRC Critical Reviews in Biomedical Engineering, 1987, 201-240, vol. 14, Issue 3.

Henry Buchwald, et al., Long-term, continuous intravenous heparin administration by an implantable infusion pump in ambulatory patients with recurrent venous thrombosis, The C. V. Mosby Co., Oct. 1980, Surgery, p. 507-516, vol. 88.

Robert Langer, New Methods of Drug Delivery, Science, Sep. 28, 1990, p. 1527-1533, vol. 249.

\* cited by examiner

METHYSERGIDE DERIVATIVES

This application claims priority under 35 U.S.C. §119(e) from U.S. Provisional Application Ser. No. 61/745,131, filed on Dec. 21, 2012 and U.S. Provisional Application Ser. No. 61/753,328, filed on Jan. 16, 2013, both of which is hereby incorporated by reference in their entirety.

FIELD

Provided herein are novel methysergide derivatives and compositions thereof. In other embodiments, provided herein are methods of treatment, prevention, or amelioration of a variety of medical disorders such as, for example, migraine and Parkinson's disease using the compounds and compositions disclosed herein. In still other embodiments, provided herein, such as, for example, are methods for antagonizing the 5-$HT_{2B}$ receptor without agonizing the 5-$HT_{2B}$ receptor using the compounds and compositions disclosed herein. In still other embodiments, provided herein such as, for example, are methods of agonizing the $5HT_{1A}$ receptor using the compounds and compositions disclosed herein.

BACKGROUND

Methysergide has superior efficacy for migraine prophylaxis and has been available commercially as oral tablets (i.e., Sansert® or Deseril®) for the treatment and/or prevention of migraine headaches. Since methysergide is a $5HT_{2B}$ antagonist, it should not have undesirable side effects such as cardiac and non-cardiac fibrosis, including cardiac valvulopathy. However, methysergide has low oral bioavailability and is metabolized in-vivo to the metabolite methylergotmetrine, which is a $5HT_{2B}$ agonist, and consequently leads to development of fibrosis (e.g., retroperitoneal fibrosis, pleuropulmonary fibrosis, subendocardial fibrosis and fibrotic thickening of cardiac valves) in many patients who use Sansert® or Deseril® for extended therapy.

Accordingly, there is a continuing need for novel methysergide derivatives which have $5HT_{2B}$ antagonist activity, superior bioavailability and are not metabolized in vivo into a $5HT_{2B}$ agonist.

SUMMARY

Provided herein are novel methysergide derivatives which address these and other needs. In one aspect, the novel methysergide derivatives compounds described herein include compounds of Formula (I) or (II):

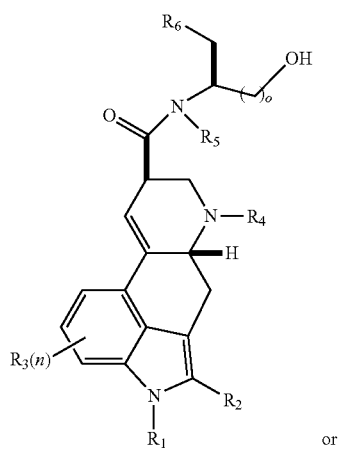

(I)

or

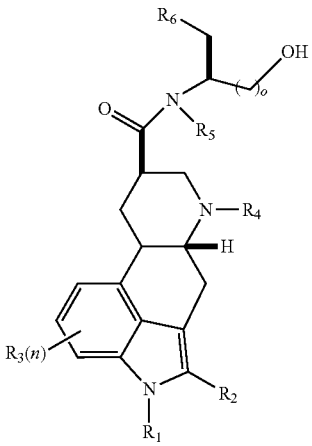

(II)

or salts, polymorphs, hydrates or solvates thereof, wherein:

$R_1$ is hydrogen, ($C_1$-$C_4$) alkyl, substituted ($C_1$-$C_4$) alkyl, ($C_1$-$C_4$) alkyl substituted with one or more fluorine atoms, ($C_1$-$C_4$) acyl, substituted ($C_1$-$C_4$) acyl, ($C_1$-$C_4$) heteroalkyl or substituted ($C_1$-$C_4$) heteroalkyl;

$R_2$ is hydrogen, ($C_1$-$C_4$) alkyl, substituted ($C_1$-$C_4$) alkyl, ($C_1$-$C_4$) alkyl substituted with one or more fluorine atoms, ($C_1$-$C_4$) acyl, substituted ($C_1$-$C_4$) acyl, halogen, —OH, ($C_1$-$C_4$) heteroalkyl or substituted ($C_1$-$C_4$) heteroalkyl;

$R_3$ is alkyl, substituted alkyl, acyl, substituted acyl, halo, heteroalkyl, substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$O_2CR_{107}$;

$R_4$ is hydrogen, ($C_1$-$C_3$) alkyl, ($C_1$-$C_3$) substituted alkyl or ($C_1$-$C_3$) alkyl substituted with one or more fluorine atoms;

$R_5$ is hydrogen, ($C_1$-$C_4$) alkyl, substituted ($C_1$-$C_4$) alkyl, ($C_1$-$C_4$) alkyl substituted with one or more fluorine atoms, ($C_1$-$C_4$) heteroalkyl or substituted ($C_1$-$C_4$) heteroalkyl;

$R_6$ is hydrogen, ($C_1$-$C_4$) alkyl, substituted ($C_1$-$C_4$) alkyl, ($C_1$-$C_3$) alkyl substituted with one or more fluorine atoms, ($C_1$-$C_4$) heteroalkyl or substituted ($C_1$-$C_4$) heteroalkyl;

n is 0, 1, 2 or 3;

o is 0, 1, 2, 3 or 4;

k is 0, 1 or 2; and $R_{100}$-$R_{107}$ are independently hydrogen, alkyl, substituted alkyl, acyl, substituted acyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

provided that both $R_1$ and $R_2$ are not hydrogen and that when $R_1$ is —$CH_3$, n is 0, o is 1, $R_4$ is —CH3, $R_5$ is hydrogen and $R_6$ is hydrogen that $R_2$ is not hydrogen.

Also provided are derivatives, including salts, esters, enol ethers, enol esters, solvates, hydrates and prodrugs of the compounds described herein. Further provided are compositions which include the compounds provided herein and a vehicle.

Methods of treating, preventing, or ameliorating medical disorders or symptoms thereof such as, for example, migraine, Parkinson's disease, nausea (e.g., emesis) are also provided herein. In practicing the methods, therapeutically effective amounts of the compounds or compositions thereof are administered to a subject.

DETAILED DESCRIPTION

Definitions

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{400}$, where $R^{400}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein, including but not limited to ion pairs, polymorphs, salts, hydrates, or solvates and any acceptable pharmaceutical formulations thereof and are intended to be within the scope of the present invention. Further, it should be understood, when partial structures of the compounds are illustrated, that brackets indicate the point of attachment of the partial structure to the rest of the molecule.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$—, =N—N=, —N=N—, —N=N—NR$^{503}$R$^{404}$, —PR$^{505}$—, —P(O)$_2$—, —POR$^{506}$—, —O—P(O)$_2$—, —SO—, —SO$_2$—, —SnR$^{507}$R$^{508}$— and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202-205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-Ray diffraction, X-Ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, B, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as 'prophylaxis.' In some embodiments, the compounds provided herein provide superior prophylaxis because of lower long term side effects over long time periods.

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvates" refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205-208 in *Polymorphism in Pharmaceutical Solids*, (Brittain, H. ed.), Marcel Dekker, Inc., New York, N.Y., 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-Ray diffraction, X-Ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, $NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups from the above lists useful for substituting other specified groups or atoms will be apparent to those of skill in the art. The substituents used to substitute a specified group can be further substituted, typically with one or more of the same or different groups selected from the various groups specified above.

"Subject," "individual" or "patient" is used interchangeably herein and refers to a vertebrate, preferably a mammal. Mammals include, but are not limited to, murines, rodents, simians, humans, farm animals, sport animals and pets.

"Treating" or "treatment" of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. In a further feature the treatment rendered has lower potential for long-term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, adsorption, distribution, metabolism and excretion etc., of the patient to be treated.

"Vehicle" refers to a diluent, excipient or carrier with which a compound is administered to a subject.

Compounds

Provided herein are methysergide derivatives of Formula (I) or (II):

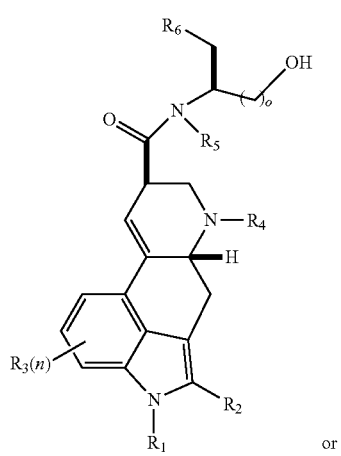

(I)

or

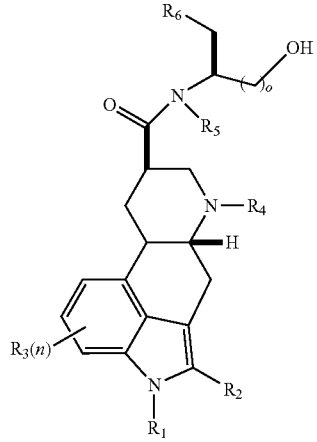

(II)

or salts, polymorphs, hydrates or solvates thereof, wherein: R$_1$ is hydrogen, (C$_1$-C$_4$) alkyl, substituted (C$_1$-C$_4$) alkyl, (C$_1$-C$_4$) alkyl substituted with one or more fluorine atoms, (C$_1$-C$_4$) acyl, substituted (C$_1$-C$_4$) acyl, (C$_1$-C$_4$) heteroalkyl or substituted (C$_1$-C$_4$) heteroalkyl; R$_2$ is hydrogen, (C$_1$-C$_4$) alkyl, substituted (C$_1$-C$_4$) alkyl, (C$_1$-C$_4$) alkyl substituted with one or more fluorine atoms, (C$_1$-C$_4$) acyl, substituted (C$_1$-C$_4$) acyl, halogen, —OH, (C$_1$-C$_4$) heteroalkyl or substituted (C$_1$-C$_4$) heteroalkyl; R$_3$ is alkyl, substituted alkyl, acyl, substituted acyl, halo, heteroalkyl, substituted heteroalkyl, —NO$_2$, —N$_3$, —OH, —S(O)$_k$R$_{100}$, —OR$_{101}$, —NR$_{102}$R$_{103}$, —CONR$_{104}$R$_{105}$, —CO$_2$R$_{106}$ or —O$_2$CR$_{107}$; R$_4$ is hydrogen, (C$_1$-C$_3$) alkyl, (C$_1$-C$_3$) substituted alkyl or (C$_1$-C$_3$) alkyl substituted with one or more fluorine atoms; R$_5$ is hydrogen, (C$_1$-C$_4$) alkyl, substituted (C$_1$-C$_4$) alkyl, (C$_1$-C$_4$) alkyl substituted with one or more fluorine atoms, (C$_1$-C$_4$) heteroalkyl or substituted (C$_1$-C$_4$) heteroalkyl; R$_6$ is hydrogen, (C$_1$-C$_4$) alkyl, substituted (C$_1$-C$_4$) alkyl, (C$_1$-C$_3$) alkyl substituted with one or more fluorine atoms, (C$_1$-C$_4$) heteroalkyl or substituted (C$_1$-C$_4$) heteroalkyl; n is 0, 1, 2 or 3; o is 0, 1, 2, 3 or 4; k is 0, 1 or 2; and R$_{100}$-R$_{107}$ are independently hydrogen, alkyl, substituted alkyl, acyl, substituted acyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; provided that both R$_1$ and R$_2$ are not hydrogen and that when R$_1$ is —CH$_3$, n is 0, o is 1, R$_4$ is —CH3, R$_5$ is hydrogen and R$_6$ is hydrogen that R$_2$ is not hydrogen.

The methysergide derivatives described herein may be used to treat, prevent, or ameliorate a variety of disorders such as, for example, migraine and Parkinson's disease using. The methysergide derivatives described herein may also be used to antagonize receptors, such as, for example, the 5-HT$_{2B}$ receptor. The methysergide derivatives described herein may also be used to agonize receptors including, but not limited to the 5-HT$_{1A}$ receptor. Further, the methysergide derivatives described herein may also be used to antagonize receptors such as dopaminergic receptors, including but not limited to dopaminergic receptor D$_{2L}$, dopaminergic receptor D$_3$ and dopaminergic receptor D$_4$.

In some embodiments, R$_2$ is hydrogen. In other embodiments, R$_1$ is (C$_1$-C$_4$) alkyl, substituted (C$_1$-C$_4$) alkyl or (C$_1$-C$_4$) alkyl substituted with one or more fluorine atoms. In still other embodiments, R$_1$ is (C$_1$-C$_4$) alkyl or (C$_1$-C$_4$) alkyl substituted with one or more fluorine atoms. In still other embodiments, R$_1$ is —CF$_3$ or —CH$_3$.

In some embodiments, $R_1$ is hydrogen. In other embodiments, $R_2$ is ($C_1$-$C_4$) alkyl, substituted ($C_1$-$C_4$) alkyl or ($C_1$-$C_4$) alkyl substituted with one or more fluorine atoms. In still other embodiments, $R_2$ is halogen, ($C_1$-$C_4$) alkyl or ($C_1$-$C_4$) alkyl substituted with one or more fluorine atoms. In still other embodiments, $R_2$ is Br, —$CF_3$ or —$CH_3$.

In some embodiments, $R_1$ and $R_2$ are not hydrogen. In other embodiments, $R_1$ is $C_1$-$C_4$) alkyl, substituted ($C_1$-$C_4$) alkyl or ($C_1$-$C_4$) alkyl substituted with one or more fluorine atoms and $R_2$ is halogen, ($C_1$-$C_4$) alkyl, substituted ($C_1$-$C_4$) alkyl or ($C_1$-$C_4$) alkyl substituted with one or more fluorine atoms. In still other embodiments, $R_1$ is $C_1$-$C_4$) alkyl, or ($C_1$-$C_4$) alkyl substituted with one or more fluorine atoms and $R_2$ is halogen, ($C_1$-$C_4$) alkyl, or ($C_1$-$C_4$) alkyl substituted with one or more fluorine atoms. In still other embodiments, $R_1$ is —$CF_3$ or —$CH_3$ and $R_2$ is Br, —$CF_3$ or —$CH_3$.

In some embodiments, $R_3$ is alkyl, acyl, halo, heteroalkyl, —$NO_2$, —OH, —$S(O)_kR_{100}$, —$OR_{101}$, —$NR_{102}R_{103}$, —$CONR_{104}R_{105}$, —$CO_2R_{106}$ or —$O_2CR_{107}$. In other embodiments, $R_3$ is alkyl, acyl, halo, heteroalkyl, —$NO_2$, —OH, —$S(O)_kR_{100}$, —$OR_{101}$, —$NR_{102}R_{103}$, —$CONR_{104}R_{105}$, —$CO_2R_{106}$ or —$O_2CR_{107}$ and n is 1. In still other embodiments, $R_3$ is alkyl, halo or —$OR_{101}$ and n is 1. In still other embodiments, n is 0.

In some embodiments, $R_4$ is hydrogen or ($C_1$-$C_3$) alkyl. In other embodiments, $R_4$ is hydrogen, methyl or allyl. In still other embodiments, $R_4$ is methyl.

In some embodiments, $R_5$ is hydrogen, alkyl or acyl. In other embodiments, $R_5$ is hydrogen or acyl. In still other embodiments, $R_5$ is hydrogen.

In some embodiments, $R_6$ is hydrogen or ($C_1$-$C_4$) alkyl. In other embodiments, $R_6$ is hydrogen. In still other embodiments, n is 0 and o is 1.

In some embodiments, $R_{100}$-$R_{107}$ are independently hydrogen, alkyl, substituted alkyl, acyl, substituted acyl, aryl, substituted aryl, arylalkyl or substituted arylalkyl. In other embodiments, $R_{100}$-$R_{107}$ are independently hydrogen, alkyl or substituted alkyl.

In some embodiments, $R_1$ is hydrogen, ($C_1$-$C_4$) alkyl or ($C_1$-$C_4$) alkyl substituted with one or more fluorine atoms, $R_2$ is hydrogen, halogen, ($C_1$-$C_4$) alkyl or ($C_1$-$C_4$) alkyl substituted with one or more fluorine atoms, $R_3$ is alkyl, acyl, halo, heteroalkyl, —$NO_2$, —OH, —$S(O)_kR_{100}$, —$OR_{101}$, —$NR_{102}R_{103}$, —$CONR_{104}R_{105}$, —$CO_2R_{106}$ or —$O_2CR_{107}$, n is 1, $R_4$ is hydrogen or ($C_1$-$C_3$) alkyl, $R_5$ is hydrogen, alkyl or acyl and $R_6$ is hydrogen or ($C_1$-$C_4$) alkyl. In other embodiments, $R_1$ is hydrogen, ($C_1$-$C_4$) alkyl or ($C_1$-$C_4$) alkyl substituted with one or more fluorine atoms, $R_2$ is hydrogen, halogen, ($C_1$-$C_4$) alkyl or ($C_1$-$C_4$) alkyl substituted with one or more fluorine atoms, $R_3$ is alkyl, halo or —$OR_{101}$, n is 1, $R_4$ is hydrogen or ($C_1$-$C_3$) alkyl, $R_5$ is hydrogen, alkyl or acyl and $R_6$ is hydrogen or ($C_1$-$C_4$) alkyl. In still other embodiments, $R_1$ is hydrogen, ($C_1$-$C_4$) alkyl or ($C_1$-$C_4$) alkyl substituted with one or more fluorine atoms, $R_2$ is hydrogen, halogen, ($C_1$-$C_4$) alkyl or ($C_1$-$C_4$) alkyl substituted with one or more fluorine atoms, n is O, $R_4$ is methyl, $R_5$ is hydrogen, and $R_6$ is hydrogen or ($C_1$-$C_4$) alkyl. In many of the above embodiments, o is 1.

In some embodiments, $R_1$ is —$CF_3$ or —$CH_3$, $R_2$ is —$CF_3$, —$CH_3$ or Br, $R_3$ is alkyl, acyl, halo, heteroalkyl, —$NO_2$, —OH, —$S(O)_kR_{100}$, —$OR_{101}$, —$NR_{102}R_{103}$, —$CONR_{104}R_{105}$, —$CO_2R_{106}$ or —$O_2CR_{107}$, n is 1, $R_4$ is methyl, $R_5$ is hydrogen and $R_6$ is hydrogen. In other embodiments, $R_1$ is —$CF_3$ or —$CH_3$, $R_2$ is —$CF_3$, —$CH_3$ or Br, $R_3$ is alkyl, halo or —$OR_{101}$, n is 1, $R_4$ is methyl, $R_5$ is hydrogen and $R_6$ is hydrogen. In still other embodiments, $R_1$ is —$CF_3$, $R_2$ is —$CF_3$, —$CH_3$ or Br, n is O, $R_4$ is methyl, $R_5$ is hydrogen and $R_6$ is hydrogen. In many of the above embodiments, o is 1.

In some embodiments, compounds having the structure of Formula (III) or Formula (IV) are provided:

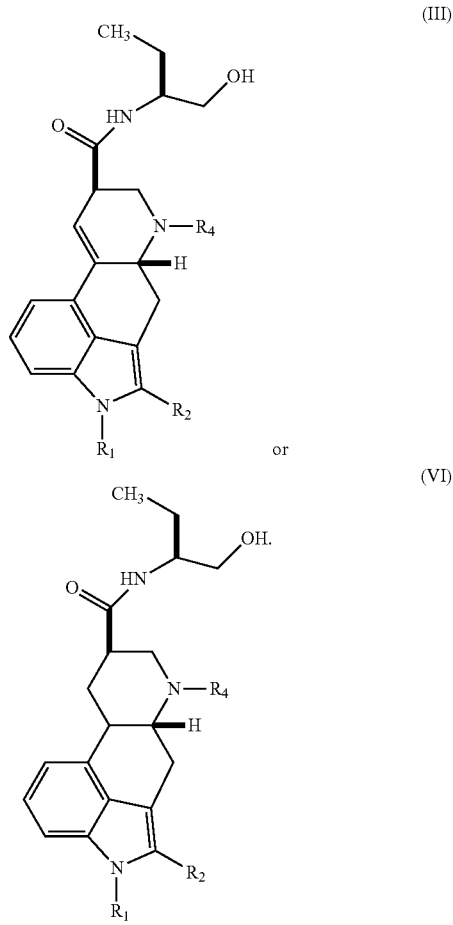

In some of the above embodiments, $R_2$ is hydrogen. In other of the above embodiments, $R_1$ is ($C_1$-$C_4$) alkyl, substituted ($C_1$-$C_4$) alkyl or ($C_1$-$C_4$) alkyl substituted with one or more fluorine atoms. In still other of the above embodiments, $R_1$ is ($C_1$-$C_4$) alkyl or ($C_1$-$C_4$) alkyl substituted with one or more fluorine atoms. In still other of the above embodiments, $R_1$ is —$CF_3$ or —$CH_3$.

In some of the above embodiments, $R_1$ is hydrogen. In other of the above embodiments, $R_2$ is halogen, ($C_1$-$C_4$) alkyl, substituted ($C_1$-$C_4$) alkyl or ($C_1$-$C_4$) alkyl substituted with one or more fluorine atoms. In still other of the above embodiments, $R_2$ is halogen, ($C_1$-$C_4$) alkyl or ($C_1$-$C_4$) alkyl substituted with one or more fluorine atoms. In still other of the above embodiments, $R_2$ is —$CF_3$, —$CH_3$ or Br.

In some of the above embodiments, $R_1$ and $R_2$ are not hydrogen. In other of the above embodiments, $R_1$ is ($C_1$-$C_4$) alkyl, substituted ($C_1$-$C_4$) alkyl or ($C_1$-$C_4$) alkyl substituted with one or more fluorine atoms and $R_2$ is halogen, ($C_1$-$C_4$) alkyl, substituted ($C_1$-$C_4$) alkyl or ($C_1$-$C_4$) alkyl substituted with one or more fluorine atoms. In still other of the above embodiments, $R_1$ is ($C_1$-$C_4$) alkyl or ($C_1$-$C_4$) alkyl substituted with one or more fluorine atoms and $R_2$ is halogen, ($C_1$-$C_4$) alkyl or ($C_1$-$C_4$) alkyl substituted with one or more fluorine atoms. In still other of the above embodiments, $R_1$ is —$CF_3$ or —$CH_3$ and $R_2$ is —$CF_3$, —$CH_3$ or Br.

In some of the above embodiments, $R_4$ is hydrogen or ($C_1$-$C_3$) alkyl. In other of the above embodiments, $R_4$ is hydrogen, methyl or allyl. In still other of the above embodiments, $R_4$ is methyl.

In some of the above embodiments, $R_1$ is hydrogen, ($C_1$-$C_4$) alkyl or ($C_1$-$C_4$) alkyl substituted with one or more fluorine atoms, $R_2$ is hydrogen, halogen, ($C_1$-$C_4$) alkyl or ($C_1$-$C_4$) alkyl substituted with one or more fluorine atoms and $R_4$ is hydrogen or ($C_1$-$C_3$) alkyl. In other of the above embodiments, $R_1$ is —$CF_3$ or —$CH_3$, $R_2$ is —$CF_3$, —$CH_3$ or Br and $R_4$ is methyl.

In some embodiments, compounds having the structure

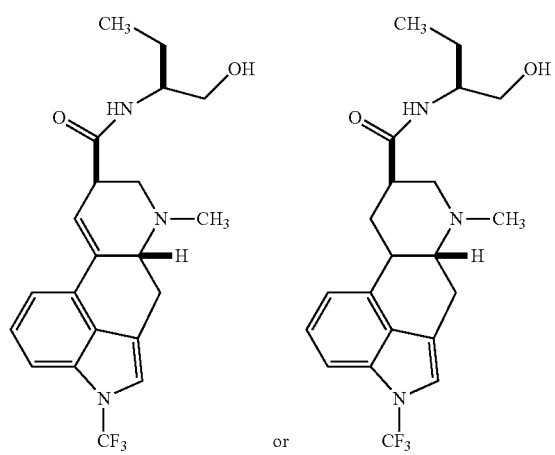 [SMILES: CC[C@@H](CO)NC(=O)[C@@H]1C=C2c3cccc4c3c(cn4C(F)(F)F)C[C@H]2N(C)C1 ; CC[C@@H](CO)NC(=O)[C@@H]1CC2c3cccc4c3c(cn4C(F)(F)F)C[C@H]2N(C)C1]

are provided. In other embodiments, compounds having the structure

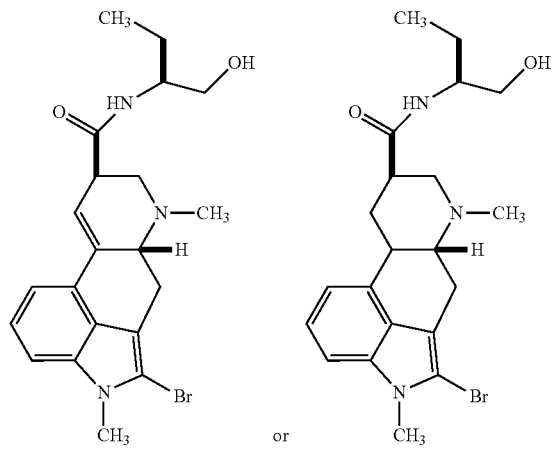

are provided. In still other embodiments, compounds having the structure

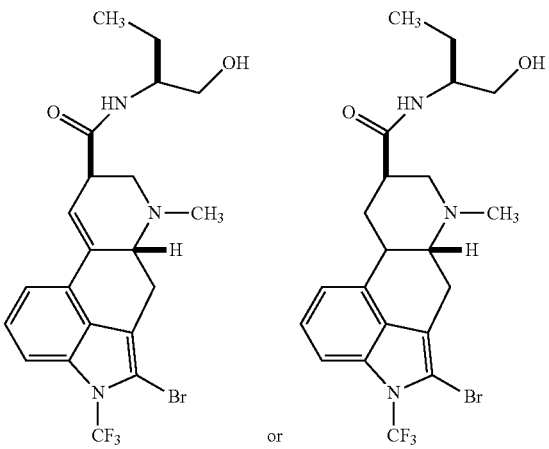 [SMILES: CC[C@@H](CO)NC(=O)[C@@H]1C=C2c3cccc4c3c(c(Br)n4C(F)(F)F)C[C@H]2N(C)C1 ; CC[C@@H](CO)NC(=O)[C@@H]1CC2c3cccc4c3c(c(Br)n4C(F)(F)F)C[C@H]2N(C)C1]

are provided. In still other embodiments, compounds having the structure

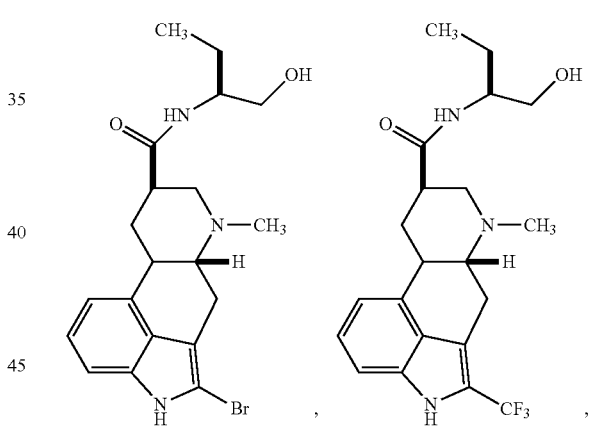

are provided. In still other embodiments, compounds having the structure

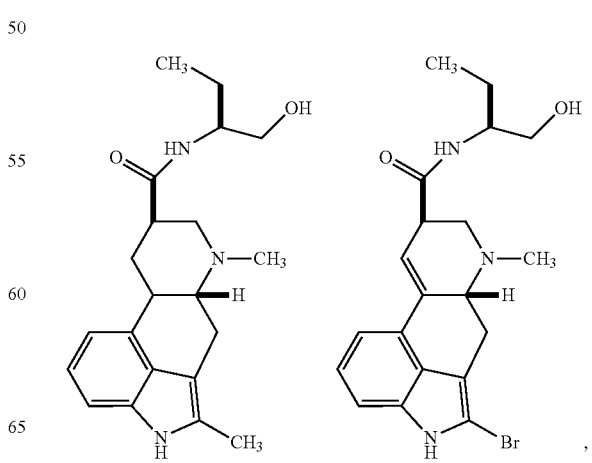

-continued

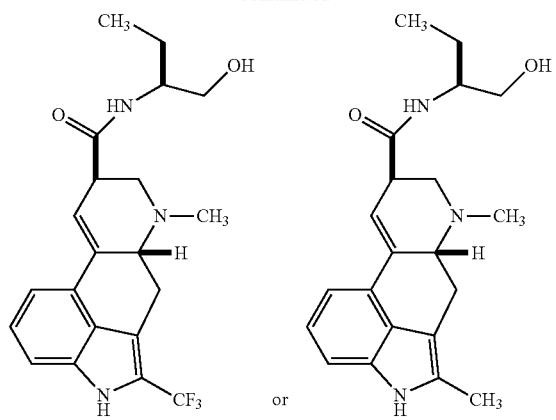

are provided. In still other embodiments, compounds having the structure

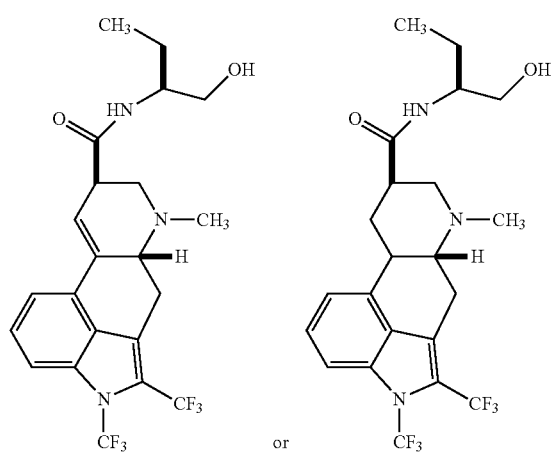

are provided. In still other embodiments, compounds having the structure

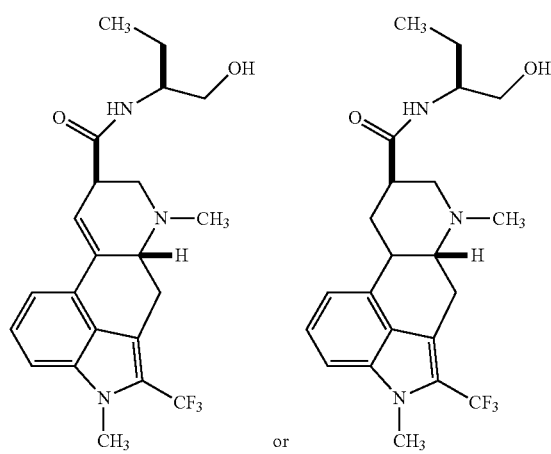 [SMILES: CC[C@@H](CO)NC(=O)[C@@H]1C=C2c3cccc4c3c(c(C)n4C(F)(F)F)C[C@H]2N(C)C1 ; CC[C@@H](CO)NC(=O)[C@@H]1CC2c3cccc4c3c(c(C)n4C(F)(F)F)C[C@H]2N(C)C1]

are provided. In still other embodiments, compounds having the structure

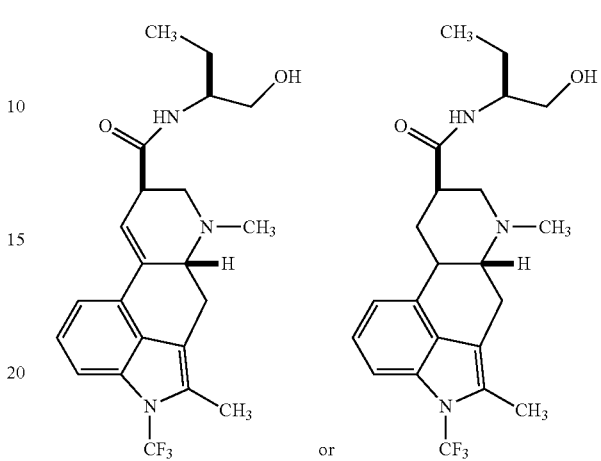

are provided. In still other embodiments, compounds having the structure

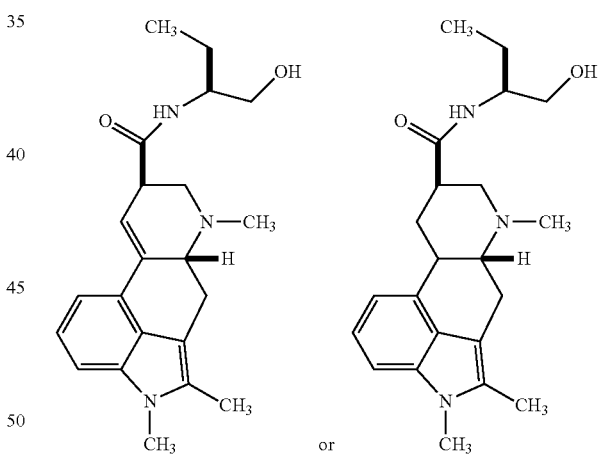

are provided.

Exemplary methods for the preparation of compounds of Formula (I) and (II) for use in the compositions and methods provided herein are described below and in the Examples but other methods known in the art can be used to prepare the novel methysergide compounds disclosed herein.

In some embodiments, direct functionalization of 2-unsubstituted analogs of compounds of Formula (I) and (II) (e.g., compounds of Formula (V) and (VI)), for example, with an alkyl halide under basic conditions can be used to provide the compounds of Formula (I) and (II).

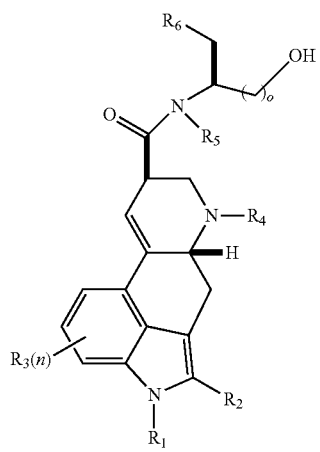
(I)

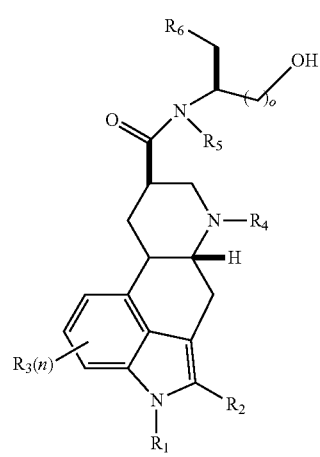
(II)

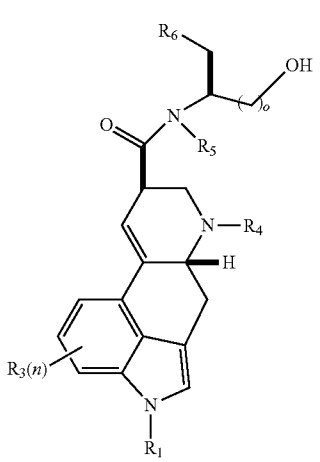
(V)

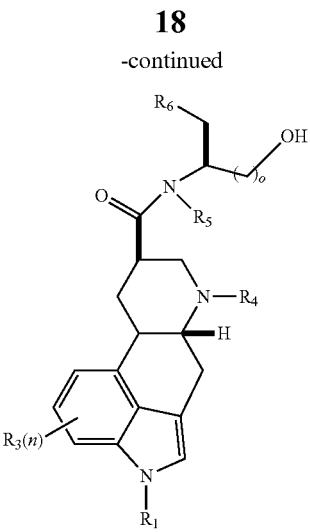
(VI)

In other embodiments, carboxylic acids (VII) and (VIII) which can be prepared by methods well known to those of skill in the art can be used provide compounds of Formulas (I) and (II).

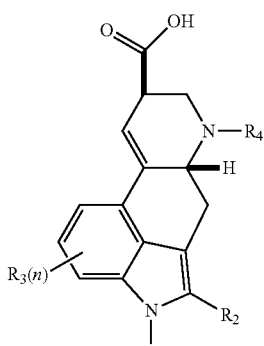
(VII)

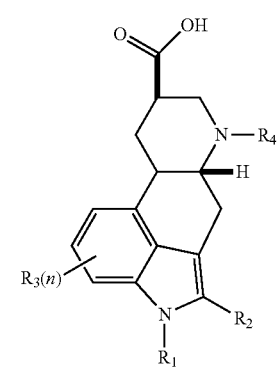
(VIII)

Many methods exist for conversion of acids (VII) and (VIII) to compounds of Formulas (I) and (II), respectively. Accordingly, preparation of (I) and (II) from carboxylic acids (V) and (VI) are well within the ambit of the skilled artisan.

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration.

In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and inhaled administration via nebulizers, pressurized metered dose inhalers and dry powder inhalers. In some embodiments, the compounds described above are formulated into compositions using techniques and procedures well known in the art (see, e.g., Ansel Introduction to Pharmaceutical Dosage Forms, Seventh Edition (1999).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some embodiments, a therapeutically effective dosage should produce a serum concentration of active ingredient of from about 0.001 ng/ml to about 50-200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e. dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the *U.S. Pharmacopeia* (USP) 25-NF20 (2002). In general, lactose-free compositions contains active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified or sustained release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref. Biomed. Eng.* 14:201 (1987); Buchwald et al., *Surgery* 88:507 (1980); Saudek et al., *N Engl. J. Med.* 321: 574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device is introduced into a subject in proximity of the site of inappropriate immune activation or a tumor. Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbital, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3. microns.

A desired ratio of inert and non-flammable HFA propellants are selected (HFA 134a (1,1,1,2-tetrafluoroethane) and HFA 227ea (1,1,1,2,3,3,3-heptafluoropropane)) and provided as a ratio to match the density of crystal particles of the compounds or derivatives. The ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The formulation of the compounds or derivatives can be administered to patients using TEMPO® (MAP Pharmaceuticals, Inc., Mountain View, Calif.), a novel breath activated metered dose inhaler. TEMPO® overcomes the variability associated with standard pressurized metered dose inhalers (pMDI), and achieves consistent delivery of drug to the lung periphery where it can be systemically absorbed. To do so, TEMPO® incorporates four novel features: 1) breath synchronous trigger—can be adjusted for different drugs and target populations to deliver the drug at a specific part of the inspiratory cycle, 2) plume control—an impinging jet to slow down the aerosol plume within the actuator, 3) vortexing chamber—consisting of porous wall, which provides an air cushion to keep the slowed aerosol plume suspended and air inlets on the back wall which drive the slowed aerosol plume into a vortex pattern, maintaining the aerosol in suspension and allowing the particle size to reduce as the HFA propellant evaporates, and 4) dose counter—will determine the doses remaining and prevent more than the intended maximum dose to be administered from any one canister.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

In human therapeutics, the physician will determine the dosage regimen that is most appropriate according to a preventive or curative treatment and according to the age, weight, stage of the disease and other factors specific to the subject to be treated. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form. The amount of active ingredient in the formulations provided herein, which will be effective in the prevention or treatment of a disorder or one or more symptoms thereof, will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject.

Exemplary doses of a formulation include milligram or microgram amounts of the active compound per kilogram of subject (e.g., from about 1 micrograms per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

Methods of treating, preventing, or ameliorating one or more symptoms of medical disorders including, for example, migraine, Parkinson's disease, vascular headaches, nausea (e.g., emesis), severe diarrhea in carcinoid syndrome are also provided herein. In practicing the methods, therapeutically effective amounts of the compounds or compositions, described herein, supra, are administered.

Migraine

Methods of treating, preventing (including prophylaxis treatment) or ameliorating one or more symptoms of migraines by administering a therapeutically effective amount of the compounds or compositions are described herein. Administration of such compounds or compositions may be performed through a variety of routes including but not limited to buccal administration, parenteral administration, oral inhalation, and nasal administration.

Many factors contribute to a compound or composition that may be suitable for treating, preventing or ameliorating one or more symptoms of migraines. Such factors include agonizing or antagonizing serotonin receptors, adrenergic receptors, and/or dopaminergic receptors. Specifically, a compound or composition that would be a good candidate for treatment of migraine symptoms or for migraine symptom prophylaxis, would selectively agonize or selectively antagonize certain serotonin receptors (also referred to as 5-HT family of receptors) and adrenergic receptors. In some embodiments, antagonism would be desirable at 5-HT$_{2B}$ receptors and adrenergic alpha$_{1A}$, alpha$_{1D}$, alpha$_{2c}$, alpha$_{2A}$ and alpha$_{2B}$ receptors using the compounds and compositions, described herein. In other embodiments, agonism would be desirable at 5-HT$_{1A}$, 5-HT$_{1B}$, 5-HT$_{1D}$, and/or 5-HT$_{1F}$ receptors. In cases where receptor antagonism is not achieved, weak or partial agonism of the 5-HT$_{2B}$ receptor is desired, but not full agonism. In some other embodiments, agonism is not desirable at the adrenergic alpha$_{1A}$, alpha$_{1D}$, alpha$_{2c}$, alpha$_{2A}$ and alpha$_{2B}$ receptors and dopaminergic receptors using the compounds and compositions described herein.

In some embodiments, methods and compounds that selectively agonize the 5-HT$_{1D}$ and 5-HT$_{1B}$ receptors are preferred. In some embodiments, methods of selectively agonizing the 5-HT$_{1D}$ receptor over the 5-HT$_{1B}$ receptor using the compounds and compositions described herein are provided. In other embodiments, the compounds and compositions described herein selectively agonizes the 5-HT$_{1D}$ receptor over the 5-HT$_{1B}$ receptor in a ratio of about 4:1. In still other embodiments, the compounds and compositions described herein selectively agonizes the 5-HT$_{1D}$ receptor over the 5-HT$_{1B}$ receptor in a ratio of about 30:1. In still other embodiments, agonistic activity of the 5-HT$_{1A}$ is preferred.

In still other embodiments, methods of reducing agonism of dopamine receptors when compared to agonism of dopamine receptors by other ergolines, such as, for example, dihydroergotamine using the compounds and compositions described herein is provided herein. In some embodiments, the dopamine receptor is the D$_2$ receptor.

Anti-Parkinson's Disease

Parkinson's disease is a degenerative disorder of the central nervous system which results in motor symptoms including shaking, rigidity, slowness of movement, difficultly walking and gait. Cognitive and behavioral symptoms are also associated with later stages of Parkinson's disease. Described below, are methods of treating, preventing or ameliorating one or more symptoms of Parkinson's disease by administering a therapeutically effective amount of the compounds or compositions described herein. Administration of such compounds or compositions may be performed through a variety of routes including but not limited to buccal administration, parenteral administration, oral inhalation, and nasal administration.

Many factors contribute to whether a compound or composition may be suitable for treating, preventing or ameliorating one or more symptoms of Parkinson's disease. Such factors include receptor modulation of adenosine receptors and dopaminergic receptors. Specifically, a compound or composition that would be useful in treating, preventing or ameliorating one or more symptoms of Parkinson's disease would have one or more of the following biological effects: (1) antagonism of adenosine receptor a2A; (2) agonism of dopaminergic D2 receptor; and (3) antagonism of dopaminergic D3 receptor.

Nausea/Anti-Emetic

Causes of nausea/vomiting can be amorphous and may have several causes. Some common causes are motion sickness, dizziness, migraine, fainting, gastroenteritis, food poisoning, stress, anxiety, exhaustion, or a side effect of a medication. Described below, are methods of treating, preventing, or ameliorating one or more symptoms of nausea or can have an anti-emetic effect by administering a therapeutically effective amount of the compounds or compositions described herein. Administration of such compounds or compositions may be performed through a variety of routes including but not limited to buccal administration, parenteral administration, oral inhalation, and nasal administration.

Many factors contribute to whether a compound or composition may be suitable for treating, preventing or ameliorating one or more symptoms of nausea or have an anti-emetic effect. Such factors include receptor modulation of neurokinin receptors, orexin receptors, serotonin receptors and dopaminergic receptors. Specifically, a compound or composition that would be useful in treating, preventing or ameliorating one or more symptoms of nausea or would have an anti-emetic effect would have one or more of the following biological effects: (1) antagonism of a neurokinin receptor, preferably antagonism of the NK1 receptor; (2) antagonism of a orexin receptor, including but not limited to OX1 and OX2; (3) antagonism of serotonin receptor 5-HT$_3$; (4) agonism of serotonin receptor 5-HT$_4$; and (5) antagonism of dopaminergic receptor D2 (including D2L), D3, and D4 receptors.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with migraine.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

It should also be understood that any suitable combination of the compounds and compositions provided herein may be used with other agents to agonize and or antagonize the receptors mentioned above.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

The following examples are provided for illustrative purposes only and are not intended to limit the scope of the invention.

EXAMPLES

Example 1

Synthesis of 2-Methylsergide

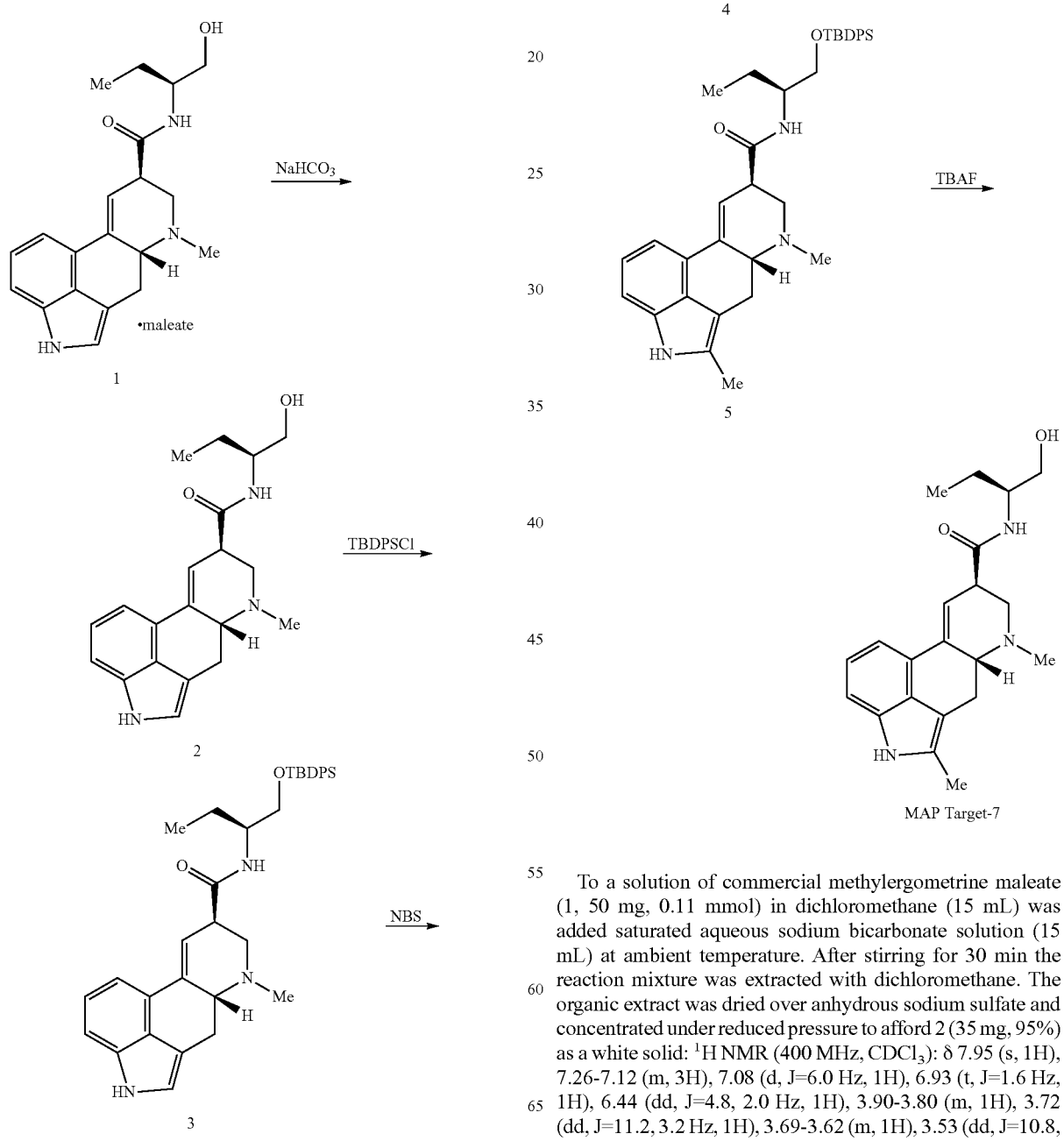

MAP Target-7

To a solution of commercial methylergometrine maleate (1, 50 mg, 0.11 mmol) in dichloromethane (15 mL) was added saturated aqueous sodium bicarbonate solution (15 mL) at ambient temperature. After stirring for 30 min the reaction mixture was extracted with dichloromethane. The organic extract was dried over anhydrous sodium sulfate and concentrated under reduced pressure to afford 2 (35 mg, 95%) as a white solid: $^1$H NMR (400 MHz, CDCl$_3$): δ 7.95 (s, 1H), 7.26-7.12 (m, 3H), 7.08 (d, J=6.0 Hz, 1H), 6.93 (t, J=1.6 Hz, 1H), 6.44 (dd, J=4.8, 2.0 Hz, 1H), 3.90-3.80 (m, 1H), 3.72 (dd, J=11.2, 3.2 Hz, 1H), 3.69-3.62 (m, 1H), 3.53 (dd, J=10.8, 6.4 Hz, 1H), 3.40-3.31 (m, 2H), 3.18 (br s, 1H), 3.06 (dd, J=11.6, 4.4 Hz, 1H), 2.85-2.74 (m, 2H), 2.60 (s, 3H), 1.65-1.40 (m, 2H), 0.95 (t, J=7.2 Hz, 3H).

Imidazole (145 mg, 2.12 mmol) followed by TBDPSCl (0.2 mL, 0.79 mmol) was added to a suspension of 2 (180 mg, 0.53 mmol) in dichloromethane (8 mL) at ambient temperature under argon atmosphere. After stirring for 8 h the reaction mixture was treated with saturated sodium bicarbonate solution and extracted with dichloromethane. The organic extract was dried over anhydrous sodium sulfate, concentrated under reduced pressure and purified by flash column chromatography (93:7 dichloromethane/methanol) to afford 3 (301 mg, 98%) as a colorless oil: $^1$H NMR (400 MHz, CDCl$_3$): δ 7.94 (s, 1H), 7.67-7.59 (m, 4H), 7.44-7.30 (m, 6H), 7.24-7.12 (m, 3H), 6.91 (t, J=1.6 Hz, 1H), 6.67 (d, J=8.8 Hz, 1H), 6.48-6.42 (m, 1H), 4.01-3.91 (m, 1H), 3.75-3.65 (m, 2H), 3.47-3.37 (m, 3H), 3.11 (dd, J=11.6, 4.8 Hz, 1H), 2.80-2.68 (m, 2H), 2.54 (s, 3H), 1.73-1.54 (m, 2H), 1.03 (t, J=2.8 Hz, 9H), 0.88 (t, J=7.6 Hz, 3H), APCI, m/z 578 [M+H]$^+$.

To a solution of 3 (301 mg, 0.52 mmol) in dichloromethane (15 mL) was added N-bromosuccinimide (93 mg, 0.52 mmol) at ambient temperature under argon atmosphere. After stirring for 20 min the reaction mixture was treated with saturated aqueous sodium bicarbonate solution and extracted with dichloromethane. The organic extract was dried over anhydrous sodium sulfate, concentrated under reduced pressure and purified by flash column chromatography (95:5 dichloromethane/methanol) to afford 4 (150 mg, 44%) as a brown oil: $^1$H NMR (400 MHz, CDCl$_3$): δ 8.14 (s, 1H), 7.68-7.59 (m, 4H), 7.45-7.31 (m, 6H), 7.16-7.05 (m, 3H), 6.59 (d, J=8.4 Hz, 1H), 6.43-6.37 (m, 1H), 4.00-3.89 (m, 1H), 3.77-3.66 (m, 2H), 3.64-3.44 (m, 2H), 3.27 (dd, J=14.4, 5.2 Hz, 1H), 3.22-3.14 (m, 1H), 2.94-2.81 (m, 1H), 2.79-2.69 (m, 1H), 2.65 (s, 3H), 1.72-1.53 (m, 2H), 1.05 (s, 9H), 0.88 (t, J=7.6 Hz, 3H) APCI, m/z 658 [M+H]$^+$.

To a solution of 4 (75 mg, 0.11 mmol) in anhydrous 1,4-dioxane (3 mL) under argon atmosphere, was added Pd(dppf)Cl$_2$ (4 mg, 0.005 mmol) followed by Zn(CH$_3$)$_2$ (22 mg, 0.22 mmol) at ambient temperature. The reaction mixture was refluxed at 110° C. for 90 minutes. After cooling to ambient temperature, the reaction mixture was quenched with MeOH (5 mL) and concentrated under reduced pressure. The residue was purified by flash column chromatography (95:5 dichloromethane/methanol) to afford 5 (30 mg, 44%) as a yellow oil: $^1$H NMR (400 MHz, CDCl$_3$): δ 7.68-7.58 (m, 5H), 7.44-7.30 (m, 6H), 7.15-7.03 (m, 3H), 6.66 (d, J=8.8 Hz, 1H), 6.44-6.38 (m, 1H), 4.00-3.90 (m, 1H), 3.75-3.65 (m, 2H), 3.45-3.35 (m, 2H), 3.28 (dd, J=14.0, 5.2 Hz, 1H), 3.11 (dd, J=11.2, 4.4 Hz, 1H), 2.71 (dd, J=11.6, 7.6 Hz, 1H), 2.65-2.55 (m, 1H), 2.56 (s, 3H), 2.38 (d, J=0.8 Hz, 3H), 1.72-1.54 (m, 2H), 1.03 (s, 9H), 0.88 (t, J=7.2 Hz, 3H), APCI, m/z 592 [M+H]$^+$.

To a solution of 5 (50 mg, 0.08 mmol) in anhydrous THF (4 mL) at 0° C. under argon atmosphere, was added TBAF (1M in THF) (0.33 mL, 0.33 mmol). After stirring 0° C. to ambient temperature over 1 h the reaction mixture was concentrated under reduced pressure. The residue was purified by flash column chromatography (85:15 dichloromethane/methanol) to afford 2-methylsergide (MAP-Target-7) (16 mg, 54%; AUC HPLC 98.67%) as a light yellow solid: $^1$H NMR (400 MHz, CDCl$_3$): δ 7.67 (s, 1H), 7.17-7.01 (m, 4H), 6.40 (dd, J=4.4, 1.6 Hz, 1H), 3.90-3.80 (m, 1H), 3.72 (dd, J=11.2, 3.6 Hz, 1H), 3.67-3.59 (m, 1H), 3.52 (dd, J=11.2, 6.4 Hz, 1H), 3.37-3.30 (m, 1H), 3.23 (dd, J=14.0, 5.2 Hz, 1H), 3.06 (dd, J=11.6, 4.4 Hz, 1H), 2.81 (dd, J=11.6, 4.8 Hz, 1H), 2.72-2.63 (m, 1H), 2.61 (s, 3H), 2.38 (d, J=0.8 Hz, 3H), 1.70-1.40 (m, 3H), 0.94 (t, J=7.2 Hz, 3H); APCI, m/z 354 [M+H]$^+$.

Example 2

Synthesis of 2-CF3-Sergide

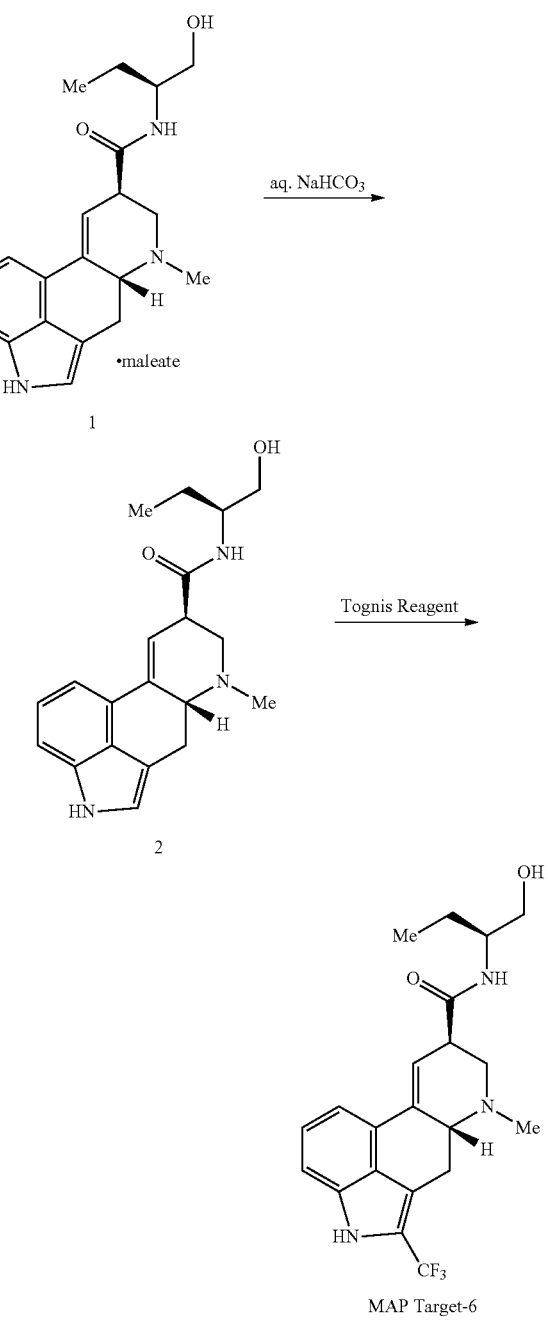

MAP Target-6

To a solution of commercial methylergometrine maleate (1, 50 mg, 0.11 mmol) in dichloromethane (15 mL) was added saturated aqueous sodium bicarbonate solution (15 mL) at ambient temperature. After stirring for 30 min the reaction mixture was extracted with dichloromethane. The organic extract was dried over anhydrous sodium sulfate and concentrated under reduced pressure to afford 2 (35 mg, 95%)

as a white solid: $^1$H NMR (400 MHz, CDCl$_3$): δ 7.95 (s, 1H), 7.26-7.12 (m, 3H), 7.08 (d, J=6.0 Hz, 1H), 6.93 (t, J=1.6 Hz, 1H), 6.44 (dd, J=4.8, 2.0 Hz, 1H), 3.90-3.80 (m, 1H), 3.72 (dd, J=11.2, 3.2 Hz, 1H), 3.69-3.62 (m, 1H), 3.53 (dd, J=10.8, 6.4 Hz, 1H), 3.40-3.31 (m, 2H), 3.18 (br s, 1H), 3.06 (dd, J=11.6, 4.4 Hz, 1H), 2.85-2.74 (m, 2H), 2.60 (s, 3H), 1.65-1.40 (m, 2H), 0.95 (t, J=7.2 Hz, 3H).

Copper (II) acetate (8.5 mg, 0.047 mmol) and Togni's reagent (89 mg, 0.28 mmol) was dissolved in MeOH (4 mL) under argon atmosphere and intermediate 2 (80 mg, 0.23 mmol) added at room temperature. The reaction mixture was heated at 40° C. for 90 minutes. It was cooled to ambient temperature, treated with saturated sodium bicarbonate solution and extracted with dichloromethane. The organic extract was dried over anhydrous sodium sulfate, concentrated under reduced pressure and purified by flash column chromatography. (92:8 dichloromethane/methanol) to give 2-CF3-sergide (MAP Target-6) (20 mg, 21%; AUC HPLC>99%) as a white solid: $^1$H NMR (400 MHz, CDCl$_3$): δ 8.16 (s, 1H), 7.35-7.23 (m, 2H), 7.20 (dd, J=7.2, 0.4 Hz, 1H), 7.11 (d, J=6.8 Hz, 1H), 6.48 (dd, J=4.4, 1.6 Hz, 1H), 3.90-3.80 (m, 1H), 3.73 (dd, J=11.2, 3.2 Hz, 1H), 3.70-3.63 (m, 1H), 3.56 (dd, J=10.8, 6.0 Hz, 1H), 3.53-3.47 (m, 1H), 3.37-3.30 (m, 1H), 3.05 (dd, J=11.6, 4.4 Hz, 1H), 2.99 (br s, 1H), 2.88-2.77 (m, 2H), 2.62 (s, 3H), 1.66-1.43 (m, 2H), 0.94 (t, J=7.6 Hz, 3H); APCI, m/z 408 [M+H]$^+$.

Example 3

Human Receptor Agonist/Antagonist Activity Screen

Receptor agonist/agonist activity assays were performed using 2-CF3-sergide. Table 1 summarizes the cell lines (CHO-K1/HEK293 transfected with relevant human receptor) and the assays performed to detect any agonist or antagonist activity.

TABLE 1

Additional Human Receptor Screen

| Receptor | Accession No. | Cell Line | Assay | Reference Agonist | Reference Antagonist |
|---|---|---|---|---|---|
| Adrenergic α$_{1A}$ | NP_000671.2 | CHO-K1 mAeq | Aequorin | A61603 | RS17053 |
| Adrenergic α$_{1B}$ | NP_000670.1 | CHO-K1 mAeq | Aequorin | Cirazoline | Quinazoline |
| Adrenergic α$_{1D}$ | NP_000669.1 | CHO-K1 mAeq | Aequorin | Cirazoline | Quinazoline |
| Adrenergic α$_{2A}$ | NP_000672.2 | CHO-K1 | GTPγ[35S] | UK14,304 | Rauwolscine |
| Adrenergic α$_{2B}$ | AAB25558 | CHO-K1 | GTPγ[35S] | Guanfacine | Rauwolscine |
| Adrenergic α$_{2C}$ | NP_000672.2 | CHO-K1 | GTPγ[35S] | UK14,304 | Rauwolscine |
| Dopamine D$_1$ | NP_000785.1 | CHO-K1 | cAMP | SKF81297 | SCH23390 |
| Dopamine D$_{2L}$ | AAB26819.1 | CHO-K1 | GTPγ[35S] | Quinpirol | Haloperidol |
| Dopamine D$_3$ | P35462 | CHO-K1 | GTPγ[35S] | Dopamine | GR 103691 |
| Dopamine D$_4$ | AAL_58637.1 | CHO-K1 | GTPγ[35S] | Dopamine | Haloperidol |
| Serotonin 5-HT$_{1A}$ | NP_000515.2 | CHO-K1 | GTPγ[35S] | 5-CT | S(way)-100135 |
| Serotonin 5-HT$_{1B}$ | NP_000854.1 | CHO-K1 | GTPγ[35S] | 5-CT | Methiotepin |
| Serotonin 5-HT$_{1D}$ | NP_000855.1 | CHO-K1 | GTPγ[35S] | 5-CT | not validated |
| Serotonin 5-HT$_{1F}$ | NP_000857.1 | CHO-K1 | cAMP | 5-HT | Methiotepin |
| Serotonin 5-HT$_{2A}$ | NP_000612.1 | CHO-K1 mAeq G$_{α16}$ | Aequorin | α-methyl-5-HT | Ketanserin |
| Serotonin 5-HT$_{2B}$ | NP_00858.2 | CHO-K1 mAeq G$_{α16}$ | Aequorin | α-methyl-5-HT | SB204741 |
| Serotonin 5-HT$_3$ | NP_00860.2 | HEK-293 mAeq | Aequorin | 5-HT | MDL72222 |
| NDMA (GRIN1) | NP_000823.4 | CHO-Kl | RLB | glycine | [3H]MDL 105,519 |
| mGluR3 | NP_000831.2 | CHO-AEQ-inducible | Aequorin | Glutamic acid | LY341495 |
| mGluR5 | NP_000833.1 | CHO-AEQ-inducible | Aequorin | Glutamic acid | MPEP |
| mGluR7 | NP_000835.1 | CHO-K1 | cAMP | L-AP4 | MMPIP |
| PAC1 | NP_001109 | CHO-AEQ | Aequorin | PACAP 38 | PACAP 6-38 |
| VPAC1 | NP_004615.2 | CHO-AEQ | Aequorin | hVIP1 | PG97-269 |
| VPAC2 | ACC41756.1 | CHO-AEQ | Aequorin | hVIP1 | Unavailable |
| CCK1 | NP_000721.1 | CHO-AEQ | Aequorin | CCK8 sulfated | PD142,898 |
| CCK2 | NP_795344.1 | CHO-AEQ | Aequorin | CCK8 sulfated | LY225910 |
| SST1 | NP_001040.1 | CHO-K1 | GTPγ[35S] | SST28 | Unavailable |
| SST2 | NP_001041.1 | CHO-K1 | GTPγ[35S] | SST28 | CYN 154806 |
| SST3 | NP_001042.1 | CHO-K1 | GTPγ[35S] | SST28 | Unavailable |
| SST4 | NP_001043.2 | CHO-K1 | GTPγ[35S] | SST28 | Unavailable |
| SST5 | NP_001044.4 | CHO-K1 | GTPγ[35S] | SST28 | Unavailable |
| AM1 | NP_005786.1 AJ001015 | CHO-K1 | cAMP | ADM (13-52) | ADM (22-52) |

TABLE 1-continued

Additional Human Receptor Screen

| Receptor | Accession No. | Cell Line | Assay | Reference Agonist | Reference Antagonist |
|---|---|---|---|---|---|
| AM2 | NP_005786.1 AJ001016 | CHO-K1 | cAMP | ADM (1-52) | ADM (22-52) |
| CGRP | NP_005786.1 NP_005846.1 | CHO-AEQ | Aequorin | Alpha CGRP | B10647603 |
| OX1 | NP_001516 | CHO-AEQ | Aequorin | Orexine A | SB334867 |
| OX2 | NP_001517 | CHO-AEQ | Aequorin | Orexine A | Hirose 29 |
| NK1 | NP_001049.1 | CHO-AEQ | Aequorin | Substance P | RP67580 |
| NK2 | AAA60347.1 | CHO-AEQ | Aequorin | NKA | SR48968 |
| NK3 | NP_001050.1 | CHO-AEQ | Aequorin | NKA | SB222200 |
| OP1 | ACG60644.1 | CHO-K1 | GTPγ[35S] | SNC80 | Naltrindol |
| OP2 | NP_000903.2 | CHO-K1 | GTPγ[35S] | U-50488 | Nor-binaltorphimine |
| OP3 | NP_001138751.1 | CHO-K1 | GTPγ[35S] | DAMGO | CTOP |
| Adenosine A2a | NP_000666.2 | HEK293 | cAMP | Neca | ZM 241385 |

Aequorin assays were conducted to monitor activity for 8'OH-2CF3-dihydroergotamine (8'OH-2CF3-DHE) against the receptors indicated in Table 1 above (except for mGlu3 and mGlu5). CHO-K1 cells coexpressing mitochondrial apoaequorin and the recombinant human receptor of interest were grown to mid-log phase in culture media without antibiotics and then detached with PBS-EDTA, centrifuged and resuspended in assay buffer (DMEM/HAM's F12 with HEPES, without phenol red+0.1% BSA, protease free) at a concentration of 1×10$^6$ cell/mL. Cells were incubated at room temperature for at least 4 hours with coelenterazine h. Reference agonist/antagonist was tested to evaluate the performance of the assay and to determine $EC_{50}/IC_{50}$.

50 μL of the cell suspension was mixed with 50 μL of test or reference agonist in a 96-well plate. The resulting emission of light was recorded using Hamamatsu Functional Drug Screening System 6000 (FDSS 6000) luminometer. For antagonist testing, 100 μL of the reference agonist at its EC80 was injected on the mix of cells and test compound, following an incubation of 15 minutes after the first injection. The resulting emission of light was r recorded using Hamamatsu Functional Drug Screening System 6000 (FDSS 6000) luminometer.

To standardize the emission of recorded light (and determine of the "100% signal") across plates and across different experiments, some wells contained 100 μM digitonin or a saturating concentration of ATP (20 μM).

For mGlu3 and mGlu5, CHO-K1 cells coexpressing mitochondrial apoaequorin and recombinant human receptor grown to mid-log phase in culture media without antibiotics and supplemented with doxycycline, (final concentration of 600 ng doxycycline/mL), was detached with PBS-EDTA, centrifuged and resuspended in assay buffer (HBSS, 2.1 mM CaCl$_2$, 3 μg/mL GPT (Glutamate-Pyruvate transaminase), 4 mM MEM Sodium Pyruvate, 0.1% BSA protease free) at a concentration of 1×10$^6$ cells/mL. Cells were incubated at room temperature for at least 4 hours with coelenterazine h. Reference agonist/antagonist was tested to evaluate the performance of the assay and to determine $EC_{50}/IC_{50}$.

For agonist testing, 30 μL of cell suspension was mixed with 30 μL of test or reference agonist in a 384-well plate. The resulting emission of light was recorded using Hamamatsu Functional Drug Screening System 6000 (FDSS 6000) luminometer. For antagonist testing 30 μL of the reference agonist at its EC80 was injected on the mix of cells and test compound, following an incubation of 3 minutes after the first injection. The resulting emission of light was recorded using Hamamatsu Functional Drug Screening System 6000 (FDSS 6000) luminometer.

cAMP HTRF (Gs) studies were conducted to monitor activity for 8'OH-2CF3-dihydroergotamine (8'OH-2CF3-DHE) against the receptors indicated in Table 1 above. Cells expressing the human recombinant receptor of interest were grown in media without antibiotic and detached by gentle flushing with PBS-EDTA (5 mM EDTA), recovered by centrifugation and resuspended in assay buffer (KRH: 5 mM KCl, 1.25 mM MgSO$_4$, 124 mM NaCl, 25 mM HEPES, 13.3 mM glucose, 1.25 mM KH$_2$PO$_4$, 1.45 mM CaCl$_2$, 0.5 g/L BSA). Dose response curves were performed in parallel with the reference compounds. For agonist tests (96-well plates), 12 μl, of cells was mixed with 12 μL of the test compound at increasing concentrations and then incubated for 30 minutes at room temperature. Lysis buffer was added and after a 1 hour incubation, cAMP concentrations was determined according to the manufacturer specification with the HTRF kit. For antagonist tests (96-well plates), 12 μL of cells was mixed with 6 μL of the test compound at increasing concentrations and then incubated for 10 minutes. 6 μl, of the reference agonist was added at a final concentration corresponding to the historical EC80. The plates were then incubated for 30 minutes at room temperature. Lysis buffer was added and after a 1 hour incubation, cAMP concentrations were determined according to the manufacturer specification, with the HTRF kit.

cAMP HTRF (Gi) studies were conducted to monitor activity for 8'OH-2CF3-dihydroergotamine (8'OH-2CF3-DHE) against the receptors indicated in Table 1 above. Cells expressing the human recombinant receptor of interest were grown in media without antibiotic and detached by gentle flushing with PBS-EDTA (5 mM EDTA), recovered by centrifugation and resuspended in assay buffer (KRH: 5 mM KCl, 1.25 mM MgSO$_4$, 124 mM NaCl, 25 mM HEPES, 13.3 mM glucose, 1.25 mM KH$_2$PO$_4$, 1.45 mM CaCl$_2$, 0.5 g/L BSA). Dose response curves were performed in parallel with the reference compounds. For agonist tests (96-well plates), 12 μL of cells was mixed with 6 μL of the test compound at increasing concentrations and 6 μL of forskolin and then incubated for 30 minutes at room temperature. Lysis buffer was added and after a 1 hour incubation, cAMP concentrations was determined according to the manufacturer specification with the HTRF kit. For antagonist tests (96-well plates), 12 μL of cells was mixed with 6 μL of the test compound at increasing concentrations and then incubated for 10 minutes. 6 µL of forskolin and reference agonist was added at a final concentration corresponding to the historical EC80. The plates were then incubated for 30 minutes at room temperature. Lysis buffer was added and after a 1 hour incubation, cAMP concentrations were determined according to the manufacturer specification, with the HTRF kit.

GTPγS studies were conducted to monitor agonist activity for 8'OH-2CF3-dihydroergotamine (8'OH-2CF3-DHE) against the receptors indicated in Table 1 above. Reagents used were the following: Assay buffer (20 mM HEPES, pH 7.4; 100 mM NaCl; 10 µg/mL saponin; 30 mM $MgCl_2$); Membranes (recombinant human receptor membrane extracts were thawed on ice and diluted in assay buffer to give 1000 µg/mL (10 µg/µL) and kept on ice); GDP (diluted in assay buffer to give 30 µM solution (3 µM final concentration); beads (PVT-WGA (Amersham, RPNQ001), diluted in assay buffer at 25 mg/mL (0.25 mg/10 µL)); GTPγ$^{35}$S (Perkin Elmer, NEG030X), diluted in assay buffer to give 0.1 nM (final concentration); and ligand (agonist/antagonist diluted in assay buffer).

Membranes were mixed with GDP (1:1) and incubated for at least 15 minutes on ice. In parallel GTPγ$^{35}$S was mixed with the beads (1:1) just before starting the reaction. The following reagents were successively added in the wells of an Optiplate (Perkin Elmer): 50 µL test compound or reference ligand, 20 µL of the membranes:GDP mix (then 15 minute incubation for antagonist test), 10 µL of reference agonist at historical EC80 (for antagonist test) or 10 µL of assay buffer (for agonist test) and 20 µL of the GTPγ$^{35}$S:beads mix. The plates were then covered with a top seal and shaken on an orbital shaker for 2 minutes and then incubated for 1 hour at room temperature. The plates were then centrifuged for 10 minutes at 2000 rpm and incubated at room temperature for 1 hour and counted for 1 min/well with a Perkin Elmer Top-Count reader.

Purinergic receptor studies were conducted to monitor activity for 8'OH-2CF3-dihydroergotamine (8'OH-2CF3-DHE) against the P2×1, P2×2, P2×3, P2X4 and P2X7 receptors. Human recombinant purinergic receptor expressing HEK293 cells were used and receptor activity was evaluated at room temperature using QPatch HT® (Sophion Bioscience A/S, Denmark) automatic parallel patch clamp system. 8'OH-2CF3-DHE was evaluated in both agonist and antagonist modes at 10 and 30 µM. Each concentration was tested in triplicates.

Studies for NMDA receptors, NR1, NR2A, NR2B, NR²C, NR2D receptor, were conducted to monitor receptor activity for 8'OH-2CF3-dihydroergotamine (8'OH-2CF3-DHE) using the Fluo-8 calcium kit and a Fluorescence Imaging Plate Reader (FLIPR$^{TETRA}$™) instrument. The following channels were evaluated: Cloned NMDA receptor (NR1/NR2A) channel (encoded by the GRIN1 and GRIN2A genes, coexpressed in HEK293 cells; Cloned NMDA receptor (NR1/NR2B) channel (encoded by the GRIN1 and GRIN2B genes, coexpressed in HEK293 cells; Cloned NMDA receptor (NR1/NR2C) channel (encoded by the GRIN1 and GRIN2C genes, coexpressed in HEK293 cells; and Cloned NMDA receptor (NR1/NR2D) channel (encoded by the GRIN1 and GRIN2D genes, transiently coexpressed in HEK293 cells.

For the agonist assessment, the effect of 8'OH-2CF3-DHE was evaluated in the absence of the positive control agonist. The signal, elicited in the presence of the agonist (100 µM Glutamic acid+20 µM Glycine), was set to 100% activation and the signal in the presence of the vehicle control ($Mg^{2+}$-free HB-PS) was set to 0% activation.

For the antagonist assessment, NR1/NR2A and NR1/NR2B was activated with the positive control agonist (100 µM Glutamic acid+20 µM Glycine). The ability of 8'OH-2CF3-DHE to inhibit the signal was examined after agonist stimulation and compared to the positive control antagonist (MK-801). The signal elicited in the presence of the positive agonist (100 µM Glutamic acid+20 µM Glycine) was set to 100 (0% inhibition) and the signal from the positive antagonist {100 µM Glutamic acid+20 µM Glycine+30 or 100 µM (+) MK-801} was set to 0 (100% inhibition).

The results of the above receptor activity tests are summarized below in Table 2. As shown in Table 2, 2-CF3-sergide has full receptor antagonism of the 5-HT$_{2B}$ receptor and agonistic activity on the 5-HT$_{1A}$ receptor. Additionally, 2-CF3-sergide also has receptor antagonism at the $D_{2L}$, $D_3$, and $D_4$ dopaminergic receptors.

TABLE 2

Receptor Activity Results

| Receptor | Activity (Agonism: $EC_{50}$; Antagonism: $IC_{50}$) |
| --- | --- |
| Adrenergic α1A | $IC_{50}$ > 10000 nM |
| Adrenergic α1B | $IC_{50}$ > 1000 nM |
| Adrenergic α1D | $IC_{50}$ 38 nM |
| Adrenergic α2A | $IC_{50}$ > 10000 nM |
| Adrenergic α2B | $IC_{50}$ > 1000 nM |
| Adrenergic α2C | $IC_{50}$ > 10000 nM |
| D1 | $EC_{50}$ 257 nM |
| D2L | $IC_{50}$ > 1000 nM |
| D3 | $IC_{50}$ > 1000 nM |
| D4 | $IC_{50}$ > 1000 nM |
| 5-HT$_{1A}$ | $EC_{50}$ 258 nM |
| 5-HT$_{1B}$ | $EC_{50}$ 128 nM |
| 5-HT$_{1D}$ | $EC_{50}$ 98 nM |
| 5-HT$_{1F}$ | $EC_{50}$ 254 nM |
| 5-HT$_{2A}$ | $EC_{50}$ 1103 nM |
| 5-HT$_{2B}$ | $IC_{50}$ 42 nM |
| 5-HT$_3$ | $IC_{50}$ > 1000 nM |
| NMDA (NR1/NR2A/NR2B/NR2C/NR2D) | N/A |
| Purinergic (P2X1/P2X2/P2X3/P2X4/P2X7) | N/A |
| Glutamate (mGlu3/mGlu5/mGlu7) | mGlu7: $EC_{50}$ 46.5 nM |
| VIP/PACAP (PAC1/VPAC/VPAC2) | Inactive |
| Cholecystokinin (CCK1/CCK2) | Inactive |
| Somatostatin (SST1~SSTS) | Inactive |
| Calcitonin (AM1/AM2) | Inactive |
| Opioid (OP1/OP2/OP3) | Inactive |
| Calcitonin (CGRP) | Inactive |
| Orexin (OX1/OX2) | Inactive |
| Neurokinin (NK1/NK2/NK3) | OP2: $IC_{50}$ > 1000 nM |
| Adenosine A2a | Inactive |

What is claimed is:
1. The compound having the structure:
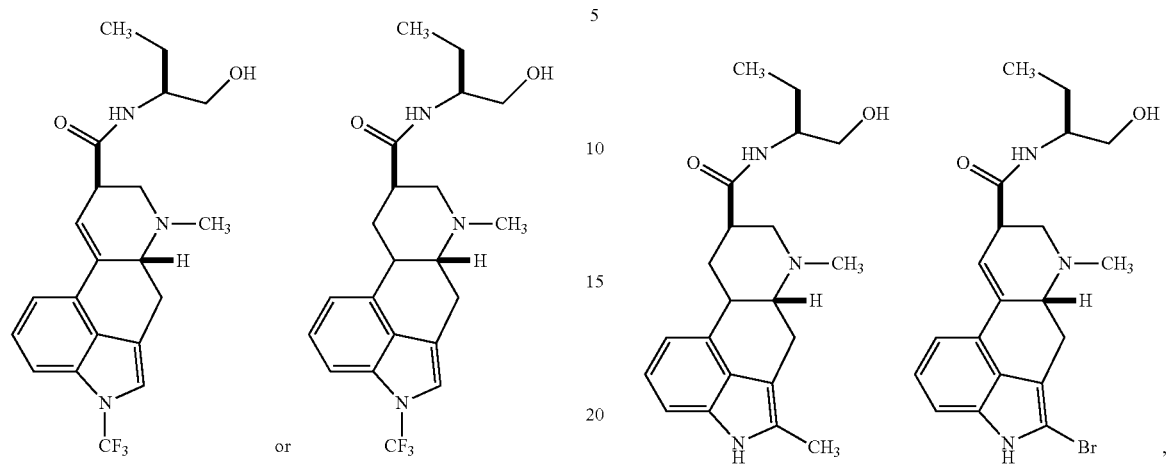
or salts thereof.
2. The compound having the structure:
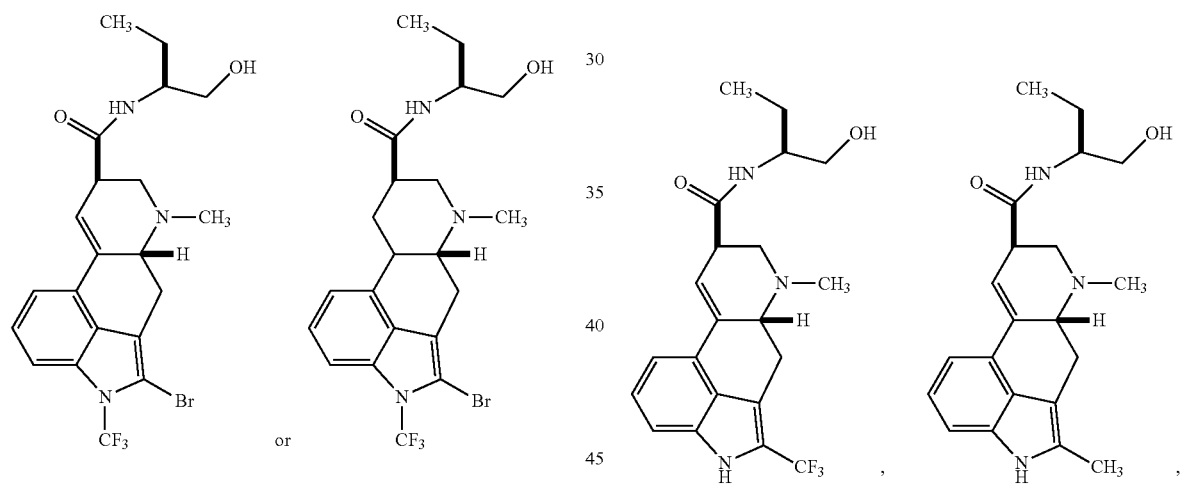
or salts thereof.
3. The compound having the structure:
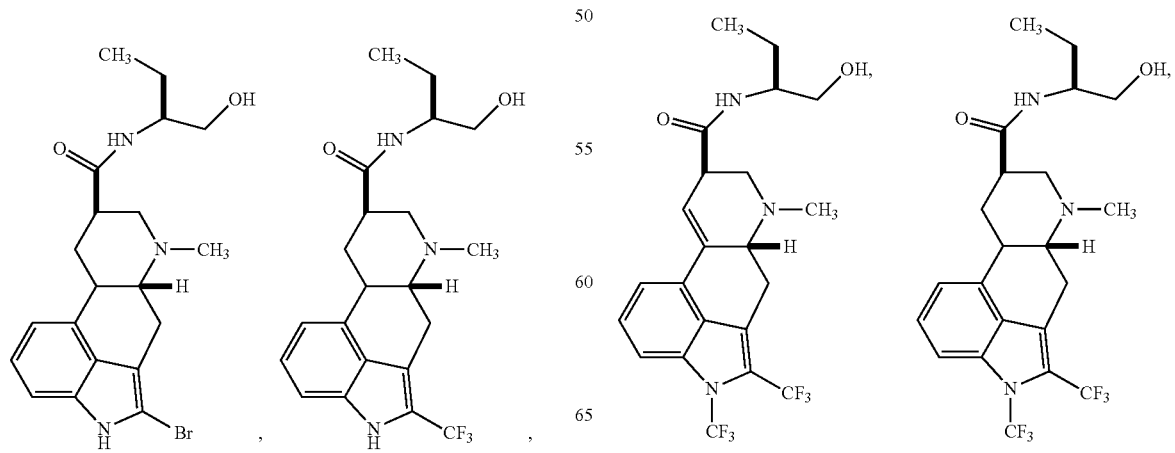

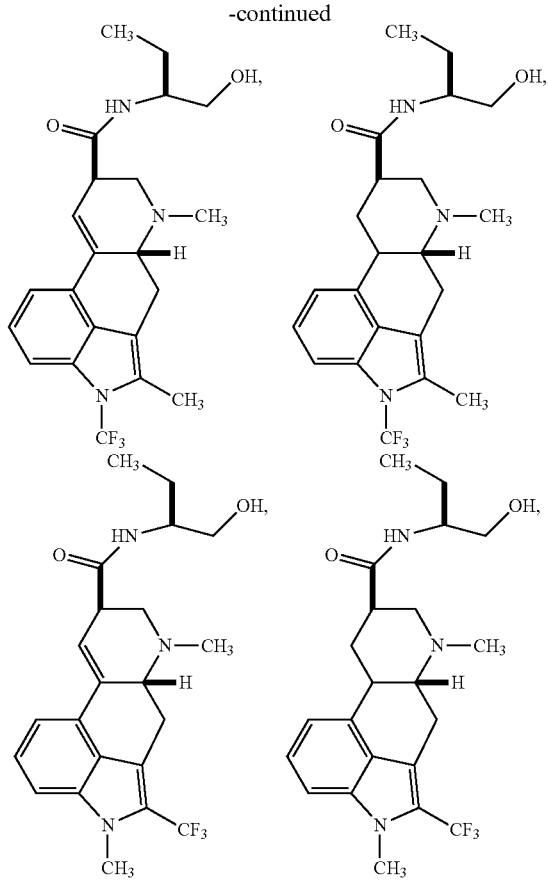
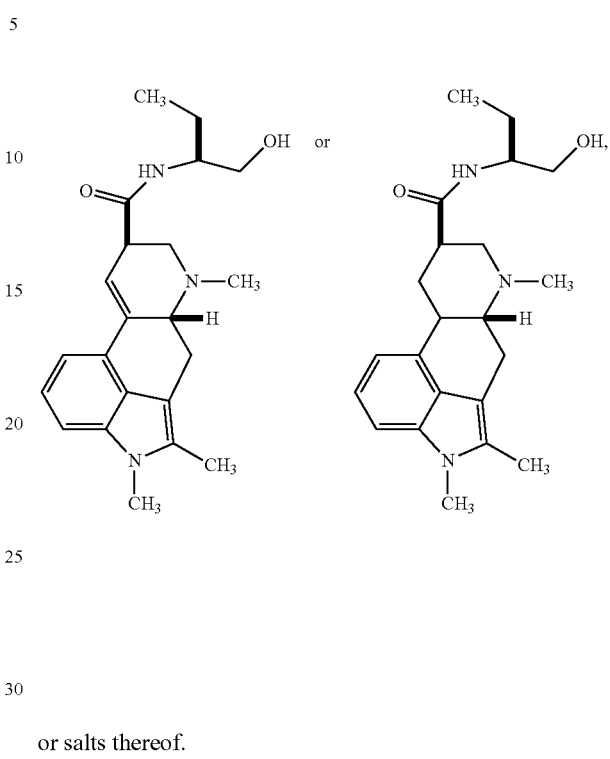
or salts thereof.
* * * * *